United States Patent

Bezwada et al.

[11] Patent Number: 5,951,997
[45] Date of Patent: Sep. 14, 1999

[54] ALIPHATIC POLYESTERS OF ε-CAPROLACTONE, P-DIOXANONE AND GYCOLIDE

[75] Inventors: Rao S. Bezwada, Whitehouse Station; Kevin Cooper, Warren; Modesto Erneta, Princeton Junction, all of N.J.

[73] Assignee: Ethicon, Inc., Somerville, N.J.

[21] Appl. No.: 08/885,714

[22] Filed: Jun. 30, 1997

[51] Int. Cl.$^6$ .......................... A61L 17/00; A61L 31/00; A61L 27/00; C08G 63/08
[52] U.S. Cl. ..................... 424/426; 424/444; 528/354
[58] Field of Search ............................. 424/426; 528/354

[56] References Cited

U.S. PATENT DOCUMENTS

| | | | |
|---|---|---|---|
| 5,080,665 | 1/1992 | Jarrett et al. | 606/219 |
| 5,252,701 | 10/1993 | Jarrett et al. | 528/354 |
| 5,314,989 | 5/1994 | Kennedy et al. | 528/354 |
| 5,475,063 | 12/1995 | Kapfan et al. | 525/411 |
| 5,502,159 | 3/1996 | Liu et al. | 528/354 |

Primary Examiner—Peter F. Kulkosky
Attorney, Agent, or Firm—Hal Brent Woodrow

[57] ABSTRACT

Absorbable, segmented polymers of aliphatic polyesters based on lactone monomers glycolide, p-dioxanone and ε-caprolactone are described. The segmented polymers exhibit a broad range of properties, especially high strength, low modulus and fast in vivo absorption, useful in a variety of medical devices. The polymers of the present invention have such properties, making them useful in medical devices for plastic surgery indications.

16 Claims, 2 Drawing Sheets

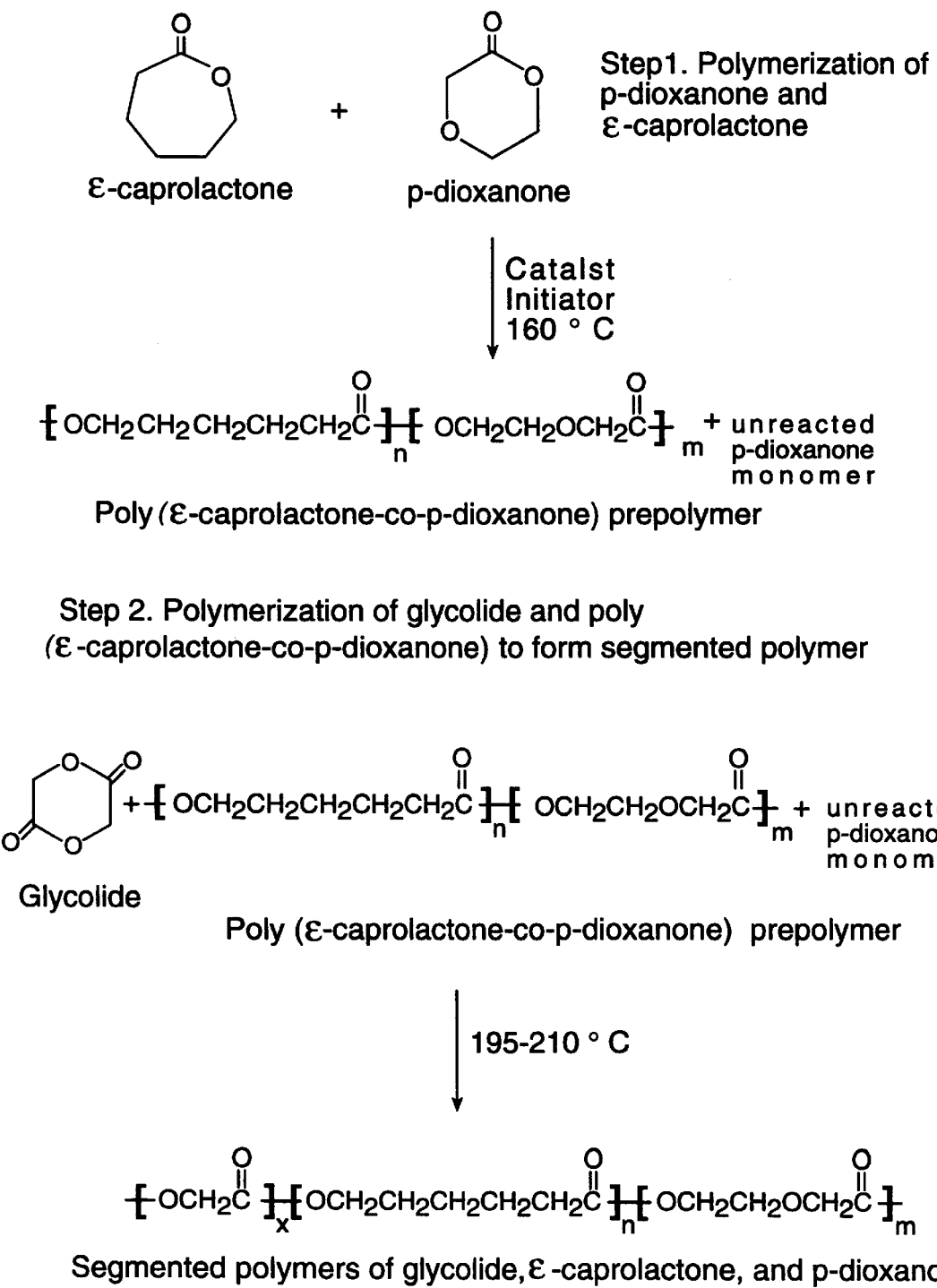
FIG. 1 Segmented polymers of Glycolide, p-Dioxanone, and ε-Caprolactone

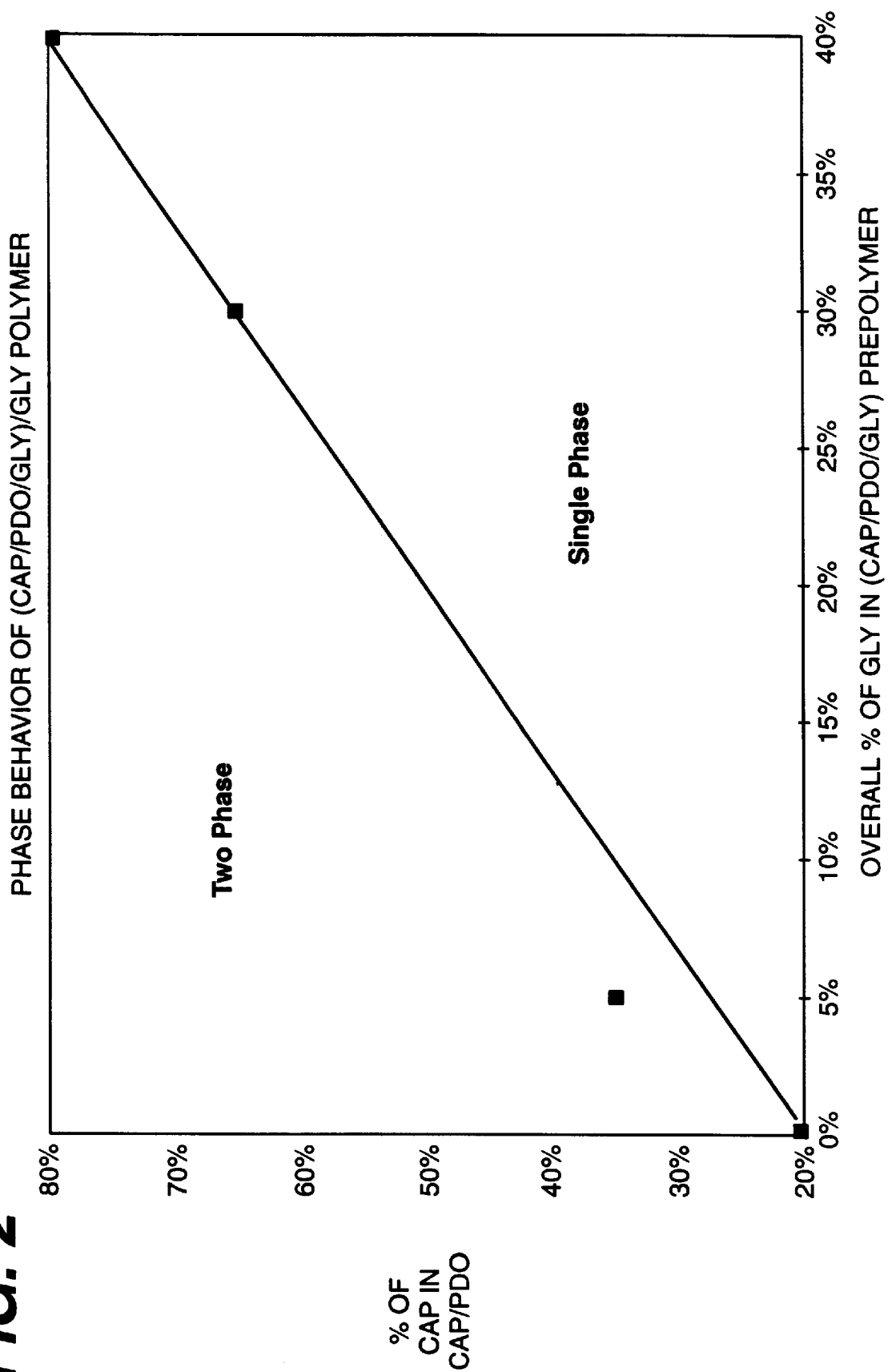

ALIPHATIC POLYESTERS OF ε-CAPROLACTONE, P-DIOXANONE AND GYCOLIDE

FIELD OF THE INVENTION

This invention relates to polymers; in particular, polymers of aliphatic polyesters of ε-caprolactone, p-dioxanone and glycolide, which are biocompatible, absorbable and well suited for the preparation of sutures.

BACKGROUND OF THE INVENTION

Synthetic absorbable biocompatible polymers are well known in the art. Such polymers are typically used to manufacture medical devices, which are implanted in body tissue and absorb over time. Synthetic absorbable biocompatible polymers include homopolymers, copolymers (random, block, segmented and graft) of monomers such as glycolic acid, glycolide (d, l, meso and mixtures thereof), lactic acid, lactide, ε-caprolactone, trimethylene carbonate and p-dioxanone. Numerous U.S. Patents describe these polymers including U.S. Pat. Nos. 5,431,679; 5,403,347; 5,314,989; 5,431,679; 5,403,347; and 5,502,159.

Block copolymers of glycolide, para-dioxanone and caprolactone have been described in the prior art. U.S. Pat. No. 5,080,665 describes deformable surgical clips or staples manufactured from block copolymers and graft copolymers having at least 50 to about 90 mole percent hard phase repeating units and the remainder being soft phase repeating units. The hard phase repeating units of the copolymer consisting of glycolic acid ester, lactic acid ester linkages and mixtures thereof. The soft phase repeating units comprising 1,3-dioxan-2-one (trimethylene carbonate), 1,4-dioxan-2-one (para-dioxanone) or ε-caprolactone linkages. These polymers are described as having a Young's modulus over 200,000, as well as a flexural strain at break of greater than about 3 percent.

Similarly, block copolymers of glycolide or lactide blocks attached to blocks containing para-dioxanone and glycolide or lactide have been described in U.S. Pat. No. 5,314,989.

Unfortunately, neither of these patents recognize that especially flexible sutures could be manufactured from a copolymer of glycolic repeating units copolymerized with a random prepolymer predominately of para-dioxanone and ε-caprolactone repeating units.

Accordingly, what is needed in this art are novel polymer compositions which have high tensile strength but low modulus, useful as, for example, sutures in plastic surgical indications.

SUMMARY OF THE INVENTION

We have discovered absorbable, biocompatible, segmented polymers of ε-caprolactone, p-dioxanone and glycolide which provides a desirable combination of tensile strength and flexibility (low modulus). The polymers are composed of about 5 mole percent to about 70 mole percent of glycolic ester repeating units which have been copolymerized with a prepolymer of about 95 mole percent to about 30 mole percent of p-dioxanone and ε-caprolactone, wherein the molar ratio of ε-caprolactone to p-dioxanone is about 95:5 to about 5:95 wherein the polymers have a Young's modulus of less than 200,000 psi.

We have additionally discovered that by preparing segmented polymers of ε-caprolactone, p-dioxanone and glycolide by a process in which ε-caprolactone and p-dioxanone or ε-caprolactone, p-dioxanone and glycolide monomers are reacted at low temperatures from about 100° C. to about 190° C. followed by reaction with glycolide at temperatures of about 160° C. to about 230° C., polymers of ε-caprolactone, p-dioxanone and glycolide can be formed with high tensile and knot fiber strength, which are extremely pliable (characterized by having a low Young's modulus). These polymers are especially well suited for making monofilaments sutures for plastic surgery indications.

Still yet a further aspect of the present invention is the polymer of the present invention which is a product of the process of the present invention.

The foregoing and other features and advantages of the invention will become more apparent from the following description and accompanying examples.

BRIEF DESCRIPTION OF THE DRAWINGS

FIG. 1 illustrates a synthetic process for the preparation of glycolide, ε-caprolactone, and p-dioxanone segmented polymers of the present invention.

FIG. 2 illustrates the relationship between the number of phases in the final polymer and the content of glycolide in the prepolymer.

DETAILED DESCRIPTION OF THE INVENTION

In theory but in no way limiting the scope of the present invention it is believed that the polymers of the present invention have sequences or arrangements of repeating units has the chemical structure shown in FIG. 1. Since each repeating segment is composed of several monomers, the polymer has very few crystalline domains and consequently the degree of crystallinity (i.e., percent) of the polymer is low. This yields a structure where a few crystalline domains act as physical crosslinks between the amorphous regions of the polymer, yielding low modulus, high strength and short BSR profiles, simialr to VICRYL®-RAPIDE® absorbable sutures (Tables 1–4). In addition, since the polymers of the present invention have low modulus, when formed into a monofilament suture their handling and tissue pass through is better than absorbable braided sutures. Block polymers would have a much greater degree of crystallinity, creating a highly crystalline material, thereby yielding very stiff, high modulus devices, especially sutures, limiting their usefulness. In applications that require pliable monofilament sutures to reduce tissue damage, such as plastic surgery, the present polymers are far superior to the polymers disclosed in the prior art.

The process of the present invention is a multi-step, one-reaction vessel, two-temperature process in which a prepolymer of p-dioxanone-co-ε-caprolactone or p-dioxanone-co-ε-caprolactone-co-glycolide, formed at low temperatures of from about 100° C. to about 190° C., preferably 160° C. for about 2 to about 8 hours, then reacted with glycolide at temperatures from about 160° C. to about 230° C. to form polymers in which segments or sequences are composed of p-dioxanone and ε-caprolactone or p-dioxanone, ε-caprolactone and glycolide, with additional glycolide repeating units at the end of the chain (FIG. 1). These segmented polymers are soft, pliable materials with low Young's modulus. Generally the Young's modulus of these polymers will be less than 200,000 psi, preferably the modulus of these polymers will be less than 185,000 psi and more preferably the modulus will be in the range of from about 150,000 psi to about 50,000 psi.

More specifically, the segmented polymers composed of glycolide, ε-caprolactone, and p-dioxanone of the present invention are prepared by a process in which p-dioxanone and ε-caprolactone or p-dioxanone, ε-caprolactone and glycolide monomers in the initial monomer feed of the polymer are reacted at low temperatures from about 100° C. to about 190° C., preferably about 160° C. to 190° C., for a sufficient time effective to cause polymerization, preferably about 2 to about 8 hours, followed by reaction with glycolide for about one-half to about 8 hours at higher temperatures of about 160° C. to about 230° C. for a sufficient time effective to cause polymerization, preferably about one-half hour to about 4 hours.

Furthermore, the segmented polymers composed of glycolide, ε-caprolactone, and p-dioxanone of the present invention will typically consist of about 5 mole percent to about 70 mole percent of repeating units of glycolide (including equivalent amounts of glycolic ester repeating units), more preferably about 10 mole percent to about 60 mole percent of repeating units of glycolide, and most preferably about 10 mole percent to about 45 mole percent repeating units of glycolide. In addition, the molar ratio of ε-caprolactone to p-dioxanone is about 95:5 to about 5:95, preferably about 90:10 to about 10:90, and most preferably about 80:20 to about 20:80. The prepolymer of ε-caprolactone and p-dioxanone generally should have an inherent viscosity in the range of from about 0.6 g/dL to about 2 g/dL and preferably will have an inherent viscosity in the range of from about 0.8 g/dL to about 1.6 g/dL.

The prepolymer may optionally contain glycolide. The glycolide in the prepolymer as shown in FIG. 2, has the effect of making the prepolymer more soluble in glycolide so that a single phase polymer can be formed. As is shown in FIG. 2 in the range of from about 0 to about 40 mole percent of glycolide can be contained in the prepolymer. Currently, it is preferred that the prepolymer contains in the range of from about 3 mole percent to about 35 mole percent glycolide (or the equivalent amount of glycolic ester repeating units). The percentage of glycolide in the prepolymer is based on the total mole percent of the polymer adding up to 100 percent.

The polymers of the present invention will typically be synthesized in a ring opening polymerization. That is, the aliphatic lactone monomers are polymerized in the presence of an organometallic catalyst and an initiator at elevated temperatures. The organometallic catalyst is preferably tin based, e.g., stannous octoate, and is present in the monomer mixture at a molar ratio of monomer to catalyst ranging from about 10,000/1 to about 100,000/1. The initiator is typically an alkanol (including diols and polyols), a glycol, a hydroxyacid, or an amine, and is present in the monomer mixture at a molar ratio of monomer to initiator ranging from about 100/1 to about 5000/1. The polymerization is typically carried out at a temperature range from about 80° C. to about 240° C., preferably from about 100° C. to about 220° C., until the desired molecular weight and viscosity are achieved.

Additionally, a minor amount (less than 5, preferably less than 3 weight percent weight percent) of additional lactone monomers selected from the group consisting of 1,3-dioxan-2-one, p-dioxanone, delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 6,6-dimethyl-dioxepan-2-one, 6,8-dioxabicycloctane-7-one and combinations of two or more thereof may be added to the either the prepolymer or with the addition of the glycolic ester repeating units of the polymer.

In one embodiment of the present invention the prepolymer of 1,4-dioxane-2-one and ε-caprolactone is polymerized in a first polymerization (optionally with a small amount of glycolide present). The polymerization is typically carried out at a temperature range from about 100° C. to about 190° C., preferably 160° C., for about 2 to about 8 hours, preferably 3 to 6 hours, yielding a p-dioxanone-co-ε-caprolactone or p-dioxanone-co-ε-caprolactone-co-glycolide prepolymer. Then, glycolide monomer is added to the prepolymer and the temperature is raised to about 160° C. to about 230° C., preferably from about 180° C. to about 210° C. for about one-half hour to about 4 hours until the desired molecular weight and viscosity are achieved. Alternatively, the glycolide could be added slowly on in discrete multiple additions to the prepolymer to improve the mixing of the monomer with the prepolymer.

Under the above described conditions, the segmented polymers composed of glycolide, ε-caprolactone, and p-dioxanone, will generally provide a weight average molecular weight of about 20,000 grams per mole to about 300,000 grams per mole, more typically about 40,000 grams per mole to about 200,000 grams per mole, and preferably about 60,000 grams per mole to about 150,000 grams per mole. These molecular weights provide an inherent viscosity between about 0.7 to about 4 deciliters per gram (dL/g), more typically about 1 to about 3.5 dL/g, and most preferably about 1 to about 3.0 dL/g as measured in a 0.1 g/dL solution of hexafluoroisopropanol (HFIP) at 25° C. Also, it should be noted that under the above described conditions, the residual monomer content will be less than about 5 weight percent.

The segmented polymers composed of glycolide, ε-caprolactone, and p-dioxanone will typically consists of about 5 mole percent to about 70 mole percent, more preferably about 10 mole percent to about 60 mole percent of glycolide repeating units, and most preferably about 10 mole percent to about 45 mole percent of glycolide repeating units. The limits lead to polymers with a desirable range of strength, stiffness and absorption profiles for use in a variety of biomedical applications. The lower limit yields polymers with a low degree of crystallinity, imparting a low modulus to fibers produced from these materials, and hence, excellent tissue pass through with less scaring (Table 4). The upper limit is the cut-off between forming a single phase polymer and a two phase blend of the terpolymer of the present invention and a homopolymer of poly(glycolide) as well as imparting a BSR profile conducive to use in plastic surgery (i.e., BSR less than 25 percent at 3 weeks).

Articles such as medical devices are molded from the segmented polymers of the present invention by use of various injection and extrusion molding equipment equipped with dry nitrogen atmospheric chamber(s) at temperatures ranging from about 140° C. to about 220° C., more preferably 180° C. to about 220° C., with residence times of about 2 to about 10 minutes, more preferably about 2 to about 5 minutes.

The polymers of the present invention can be melt processed by numerous methods to prepare a vast array of useful devices. These materials can be injection or compression molded to make implantable medical and surgical devices, including wound closure devices. The preferred devices are suture anchor devices, adhesion prevention films and hemostatic foam barriers.

Alternatively, the segmented polymers can be extruded to prepare fibers. The filaments thus produced may be fabricated into sutures or ligatures, attached to surgical needles, packaged, and sterilized by known techniques. The materials of the present invention may be spun as multifilament yarn and woven or knitted to form sponges or gauze, (or nonwoven sheets may be prepared) or used in conjunction with other molded compressive structures such as prosthetic devices within the body of a human or animal where it is desirable that the structure have high tensile strength and desirable levels of compliance and/or ductility. Useful embodiments include tubes, including branched tubes, for artery, vein or intestinal repair, nerve splicing, tendon splicing, sheets for tying up and supporting damaged surface abrasions, particularly major abrasions, or areas where the skin and underlying tissues are damaged or surgically removed. Most especially, suture applications where monofilament suture with less tissue drag, lower modulus and short BSR profiles are needed. Most especially in plastic surgery applications, where shorter absorption times and better tissue pass through would lead to better tissue fixation and less scaring.

Additionally, the segmented polymers can be molded to form films which, when sterilized, are useful as adhesion prevention barriers.

In another embodiment of the present invention, the inventive polymers may also be used as coatings for sutures and the like to improve the knot strengths and the tiedown properties, as well as to reduce the tissue drag of sutures. Conventional coating procedures can be used to apply the coating to sutures. A preferred method of applying the coating is to continuously pull the suture to be coated through a solution containing in the range of from about 1 to about 20 weight percent polymer. The suture is pulled through the coating solution in a vertical direction to insure uniform drainage. The freshly coated fiber would then be pulled continuously through a drying tunnel, taken up on a wind-up wheel and vacuum dried overnight at room temperature.

This coating is ideally suited for applying to braided sutures, since braided sutures generally have chattery or rough tie-down properties. The coating may be applied to monofilament or braided absorbable or nonabsorbable sutures. Suitable absorbable sutures may be made from naturally derived materials including but not limited to catgut and collagen, or from synthetic absorbable materials including but not limited to homopolymers of glycolide, L-lactide, $\epsilon$-caprolactone, and 1,4-dioxan-2-one and copolymers of glycolide, L-lactide, D,L-lactide, e-caprolactone, 1,3-dioxan-2-one, 1,4-dioxan-2-one, 1,5-dioxepan-2-one and 1,4-dioxepan-2-one. Suitable nonabsorbable sutures may be made from naturally occurring, nonabsorbable materials including but not limited to silk, cotton, and linen or synthetic nonabsorbable materials including but not limited to polyesters, polyamides (e.g., nylon, nylon 6, nylon 66 etc.), and polyolefins (e.g., polyethylene and polypropylene).

Sutures coated with the polymers of this invention are desirable because they have a more slippery feel, thus making it easier for the surgeon to slide a knot down the suture to the site of surgical trauma. In addition, the suture can be passed more easily through body tissue thereby reducing tissue trauma. These advantages are exhibited in comparison to sutures which do not have their surfaces coated with the polymer of this invention. In this particular application (suture coating), it may be advantageous to use polymers with low molecular weights including copolymers having inherent viscosities in the range of 0.15 dL/g to 0.75 dL/g in a 0.1 g/dL solution of HFIP at 25° C.

In another embodiment of the present invention, the polymers can be used to coat surgical needles in order to facilitate passage through tissue. The amount of coating applied to the surface of the needle is an amount which creates a layer with a thickness ranging preferably between about 2 to about 20 microns, more preferably between about 4 to about 8 microns. If the amount of coating on the needle were such that the thickness of the coating layer was greater than about 20 microns, or if the thickness was less than about 2 microns, then the desired performance of the needle as it is passed through tissue may not be achieved.

In another embodiment of the present invention, the polymers can be used as a drug delivery matrix. To form this matrix, the polymer would be mixed with a therapeutic agent. The variety of different therapeutic agents which can be used in conjunction with the polymers of the present invention is vast. In general, therapeutic agents which may be administered via the pharmaceutical compositions of the invention include, without limitation: antiinfectives such as antibiotics and antiviral agents; analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

The drug delivery matrix may be administered orally, parenterally, subcutaneously, vaginally or anally. Matrix formulations may be formulated by mixing one or more therapeutic agents with the polymer. The therapeutic agent, may be present as a liquid, a finely divided solid, or any other appropriate physical form. Typically, but optionally, the matrix will include one or more additives, such as diluents, carriers, excipients, stabilizers or the like.

The amount of therapeutic agent will depend on the particular drug being employed and medical condition being treated. Typically, the amount of drug represents about 0.001% to about 70%, more typically about 0.001% to about 50%, most typically about 0.001% to about 20% by weight of the matrix.

The quantity and type of polymer incorporated into the drug delivery matrix will vary depending on the release profile desired and the amount of drug employed. The product may contain blends of polymer to provide the required release profile or consistency to a given formulation.

Upon contact with body fluids, the polymer undergoes gradual degradation (mainly through hydrolysis) with concomitant release of the dispersed drug for a sustained or extended period. This can result in prolonged delivery (over, say 1 to 5,000 hours, preferably 2 to 800 hours) of effective amounts (say, 0.0001 mg/kg/hour to 10 mg/kg/hour) of the drug. This dosage form can be administered as is necessary depending on the subject being treated, the severity of the affliction, the judgment of the prescribing physician, and the like.

Individual formulations of drug and polymer may be tested in appropriate in vitro and in vivo models to achieve the desired drug release profile. For example, a drug could be formulated with a polymer and orally administered to an animal. The drug release profile could then be monitored by appropriate means such as, by taking blood samples at specific times and assaying the samples for drug concentration. Following this or similar procedures, those skilled in the art will be able to prepare a variety of formulations.

Furthermore, the segmented polymers of the present invention can be processed by conventional techniques to form foams, which are useful as hemostatic barriers, bone substitutes, and tissue scaffolds.

In more detail, the surgical and medical uses of the filaments, films, foams and molded articles of the present invention include, but are not necessarily limited to knitted products, woven or non-woven, and molded products including:

a. burn dressings
b. hernia patches
c. medicated dressings
d. fascial substitutes
e. gauze, fabric, sheet, felt or sponge for liver hemostasis
f. gauze bandages
g. arterial graft or substitutes
h. bandages for skin surfaces
i. burn dressings
j. bone substitutes
k. needles
l. intrauterine devices
m. draining or testing tubes or capillaries
n. surgical instruments
o. vascular implants or supports
p. vertebral discs
q. extracorporeal tubing for kidney and heart-lung machines
r. artificial skin and others
s. stents
t. suture anchors
u. injectable defect fillers
v. preformed defect fillers
w. tissue adhesives and sealants
x. bone waxes
y. cartilage replacements
z. hemostatic barriers
aa. tissue scaffolds
bb. monofilament and braided sutures.

The following non-limiting examples are illustrative of the principles and practice of this invention. Numerous additional embodiments within the scope and spirit of the invention will become apparent to those skilled in the art.

EXAMPLES

The examples describe new segmented polymers composed of glycolide, ε-caprolactone, and p-dioxanone, potentially useful as biomedical devices.

In the synthetic process, the high molecular weight aliphatic segmented polyesters are prepared by a method consisting of reacting p-dioxanone and ε-caprolactone via a ring opening polymerization at temperatures of 100° C. to 160° C. for 2 to 8 hours under an inert nitrogen atmosphere, followed by reaction with glycolide at temperatures of 160° C. to 230° C. for about one-half hour to about 4 hours until the desired molecular weight and viscosity are achieved.

In the examples which follow, the segmented polymers and monomers were characterized for chemical composition and purity (NMR, FT-IR), thermal analysis (DSC), melt rheology (melt stability and viscosity), molecular weight (inherent viscosity), and baseline and in vitro mechanical properties (Instron stress/strain). $^1$H NMR was performed on a 300 MHz NMR using $CDCl_3$ or HFAD as a reference. Thermal analysis of segmented polymers and monomers was performed on a Dupont 912 Differential Scanning Calorimeter (DSC) at a heating rate of 10° C./min. A Fisher-Johns melting point apparatus was also utilized to determine melting points of monomers. Thermal gravimetric analysis was performed on a Dupont 951 TGA at a rate of 10° C./min. under a nitrogen atmosphere. Isothermal melt stability of the segmented polymers was also determined by a Rheometrics Dynamic Analyzer RDA II for a period of 1 hour at temperatures ranging from 160° C. to 230° C. under a nitrogen atmosphere.

Inherent viscosities (I.V., dL/g) of the segmented polymers were measured using a 50 bore Cannon-Ubbelhode dilution viscometer immersed in a thermostatically controlled water bath at 25° C. utilizing chloroform or HFIP as the solvent at a concentration of 0.1 g/dL.

Melt viscosity was determined utilizing a Rheometrics Dynamic Analyzer RDA II at temperatures ranging from 160° C. to 230° C. at a rate of 1° C./min. to 10° C./min. at frequencies of $1\ s^{-1}$ to $100\ s^{-1}$ under a nitrogen atmosphere.

Fibers were prepared by a method as described in U.S. Pat. No. 4,643,191. The polymers were melt extruded in a conventional manner using an INSTRON capillary rheometer or single screw extruder. Rheometer packing temperatures ranged from about 100° C. to about 200° C. with dwell times of about 5 to about 15 minutes and ram speeds of about 1 to about 3 cm/min. Extrusion temperatures ranged from about 130° C. to about 230° C.

The extrudate was typically drawn at a draw rate of 4 feet per minute in a single or multistage drawing process with drawing temperatures of about 30° C. to about 80° C., giving a final draw ratio of about 3 to about 10.

Fibers were also annealed under similar conditions as described in U.S. Pat. No. 4,643,191. Annealing temperatures were from about 40° C. to about 120° C., preferably 90° C., with annealing times of about 2 hour to about 24 hours, preferably about 3 to 12 hours.

In vitro studies were determined in a phosphate buffer solution (pH=7.27) at a temperature of 37° C. for periods of 4, 7, 14, 21, and 28 days. Fibers (8 to 10, 6 to 12 inches long) were placed in 100 mL of buffer solution.

Several synthesis examples will be described in the following few pages. Parts and percentages where used are parts and percentages as specified as weight or moles.

Examples 1

Synthesis of a segmented polymer composed of ε-caprolactone and p-dioxanone at a 33:67 (mol/mol) composition with 55 mole % glycolide where the center segment is ε-caprolactone, p-dioxanone and glycolide, with end segments of glycolide Into a reactor provided with stirrer and jacket with heating medium is charged 284.46 grams (2.45 moles) of glycolide, 1,499.89 grams (14.7 moles) of p-dioxanone, 839.16 grams (7.35 moles) of ε-caprolactone, 2.93 mL of diethylene glycol and 3.16 mL of a 0.33 molar solution of stannous octoate in toluene. The reactor is put under vacuum and the vacuum is broken with nitrogen. The vacuum and nitrogen vacuum breaking step is repeated once more. The heating medium temperature is then raised to 190° C. for two hours, then lowered to 170° C. for 1 hour, then to 140° C. for an additional hour. 2,844.56 grams (24.507 moles) of molten glycolide is then added and the temperature is increased to 202° C. The reaction is exothermic and the batch temperature surpasses the heating medium temperature. This event is designated as the exotherm crossover. The reaction is terminated 40 minutes after the exotherm crossover. The polymer is discharged, ground and dried under vacuum for 18 hours at room temperature, followed by 24 hours at 107° C.

The molar composition of the polymer by $^1$H NMR analysis was poly(caprolactone) PCL/poly(p-dioxanone) PDO/poly(glycolide) PGA 15/25/60. The weight average molecular weight (Mw) of the polymer was 83,000 and the inherent viscosity in hexafluoroisopropanol at a solution concentration of 0.1 g/dL was 1.57 dL/g. The melting point by DSC was 204° C. The heat of fusion was 47 J/g, with hot stage microscopy showing a majority of the sample crystallizing at 165–168° C.

The polymer was extruded into a monofilament suture using an extruder at 210° C., a pressure of 1,500 psi rotating at 5 RPM with melt entering a positive displacement pump operating at 215° C. with discharge through a 50 mil. hole die into a water quench bath at 10° C.

The filament exits the bath roll at a speed of 12 feet per minute. It is then drawn with a single roll operating at 20 feet per minute, followed by drawing by roll A operating at 22 feet per minute and roll B at 150 feet per minute. It passes through a convection oven at 149° C. while being drawn by roll C operating at 165 feet per minute and it is taken up on a winder. The unannealed fiber had the properties shown in Table 1.

TABLE 1

| diam. mils | straight tensile (lbs) | straight stress Kpsi | knot tens. lbs | knot tensile (Kpsi) | Young mod. Kpsi | Elon. % |
|---|---|---|---|---|---|---|
| 14 | 18.14 | 117.9 | 9.86 | 64.05 | 134.3 | 26.4 |

The extruded fiber was annealed under nitrogen for six hours at 90° C. without relaxation at a ramp rate of 90° C. per hour. The properties after annealing are shown in Table 2.

TABLE 2

| diam. mils | straight tensile (lbs) | straight stress Kpsi | knot tens. lbs | knot tensile (Kpsi) | Young mod. Kpsi | Elon. % |
|---|---|---|---|---|---|---|
| 14.48 | 18.62 | 113.100 | 10.44 | 63.520 | 179.0 | 27.2 |

Another set of fibers was annealed for six hours at 90° C. with 10% relaxation (Table 3).

TABLE 3

| diam. mils | straight tensile (lbs) | straight stress Kpsi | knot tens. lbs | knot tensile (Kpsi) | Young mod. Kpsi | Elon. % |
|---|---|---|---|---|---|---|
| 15 | 18.53 | 104.900 | 8.29 | 46.920 | 125.3 | 34.7 |

In vitro breaking strength retention (BSR) was also determined. After immersion in buffer solution for 12 days at 40.9° C. the tensile strength dropped from 18.6 lbs down to 4.81 lbs, giving a BSR of 25.8%.

Example 2

Synthesis of a segmented polymer composed of ε-caprolactone and p-dioxanone at a 32:ε(mol/mol) composition with 55 mole % glycolide where the center segment is ε-caprolactone, and p-dioxanone, with end segments of glycolide Into a reactor provided with stirrer and jacket with heating medium is charged 822.79 grams (7.21 moles) of ε-caprolactone, 1,562.47 grams (15.32 moles) of p-dioxanone, 3.42 mL of diethylene glycol and 3.16 mL of a 0.33 molar solution of stannous octoate in toluene. The reactor is put under vacuum and the vacuum is broken with nitrogen. The vacuum and nitrogen vacuum breaking step is repeated once more. The heating medium temperature is raised to 185° C. for 1½ hours, then lowered to 160° C. for an 1 hour, then decreased to 140° C. for an additional hour. 784.42 grams (6.758 moles) of molten glycolide is added and the temperature is increased to 190° C. After ½ hour, the heating medium temperature is increased to 204° C. and 1,830.32 grams (15.76 moles) of molten glycolide is added. The reaction is exothermic and the batch temperature surpasses the heating medium temperature. This event is designated as the exotherm crossover. The reaction is terminated 45 minutes after the exotherm crossover. The polymer is discharged, ground and dried under vacuum for 18 hours at room temperature, followed by 24 hours at 110° C.

The molar composition of the polymer by $^1$H NMR analysis was PCL/PDO/PGA 16/28/56. The weight average molecular weight (Mw) of the polymer was 58,000 and the inherent viscosity in hexafluoroisopropanol at a solution concentration of 0.1 g/dL was 1.24 dL/g. The melting point by DSC was 195° C., with hot stage microscopy revealing a 1 phase system.

Size 4-0 filaments/sutures were made in a two step extrusion/orientation process as shown below:

| | |
|---|---|
| Extrusion | |
| Ram Speed, cm/min | 2 |
| Shear Rate, (1/sec) | 212.6 |
| Packing Temp., °C. | 160 |
| Run Temperature | 215 |
| App Visc., Poise | 31,719 |
| Residence Time, sec. | 600 |
| Bath conditions | ice water |
| Take Up (ft/min) | 24 |
| Orientation | |
| Draw input speed, ft/min | 4 |
| 1st draw ratio/Temp. C. | 5/45 |
| Output speed, ft/min | 20 |
| Input tension, grams | 260 |
| 2nd draw ratio/temp. | 1.4/65 |
| Input Draw Tens., grams | 580 |
| Output draw Tension,g | 600 |
| Overall draw ratio | 7 |
| Fiber Properties | |
| Av. Diameter, mils | 7.9 |
| Straight tens, lbs | 4.3 |
| Knot tens, lbs | 3.2 |
| Str. tensile, kpsi | 87.2 |
| Knot tensile, kpsi | 65.5 |
| % elongation | 41.3 |
| Modulus, kpsi | 56.9 |

Samples annealed at 0% relaxation, 90° C. for 6 hours had an average tensile strength of 4.3 pounds. The average tensile strength after immersion in buffered solution for 12 days at 40.9° C. was 0.52 pounds, giving a breaking strength retention of 12%.

Example 3

Synthesis of a segmented polymer composed of ε-caprolactone and p-dioxanone at a 20:80 (mol/mol) composition with 40 mole % glycolide where the center segment is ε-caprolactone, and p-dioxanone, with end segments of glycolide To a flame dried 250 mL two neck flask, 13.7 gm (0.12 mole) of ε-caprolactone, 49.0 gm (0.48 mole) of p-dioxanone, 0.114 mL (1.2 mmole/mole of total monomer) of diethylene glycol and 0.067 mL of stannous octoate (0.33 molar solution in toluene) were added. The flask was fitted with a flame dried mechanical stirrer and an adapter. The reactor was then purged three times before being vented with nitrogen. The reaction mixture was then heated to 160° C. under for about 2 hours. A sample was taken for characterization and the bath temperature was lowered to 110° C. for 6 hours. A second sample was taken for characterization. 46.4 gm (0.40 mole) of molten glycolide was then added to the prepolymer in the reaction flask. The temperature was then raised to 200° C. for one hour.

The polymer was isolated, ground, and dried for 16 hours at 80° C. under vacuum (0.1 mm Hg), followed by 32 hours at 110° C. to remove residual monomers. A weight loss of 5.4% was observed.

The polymer had a melting point of about 176° C. by DSC, and an inherent viscosity of 1.56 dL/g in HFIP.

Example 4

Synthesis of a segmented polymer composed of ε-caprolactone and p-dioxanone at a 75:25 (mol/mol) composition with 67 mole % glycolide where the center segment is ε-caprolactone, p-dioxanone and glycolide, with end segments of glycolide To a flame dried 250 mL two neck flask, 28.5 gm (0.25 mole) ε-caprolactone, 32.6 gm (0.281 mole) of glycolide, 9.6 gm (0.094 mole) of p-dioxanone, 0.114 mL (1.2 mmole/mole of total monomer) of diethylene glycol and 0.067 mL of stannous octoate (0.33 molar solution in toluene) were added. The flask was fitted with a flame dried mechanical stirrer and an adapter. The reactor was then purged three times before being vented with nitrogen. The reaction mixture was then slowly heated to 190° C. under nitrogen for about 16.5 hours. A second sample was taken for characterization. 43.5 gm (0.375 mole) of molten glycolide was then added to the prepolymer in the reaction flask. The temperature was then raised to 210° C. to dissolve the prepolymer in glycolide and then lowered the bath temperature to 190° C. for one hour.

The polymer was isolated, ground, and dried for 16 hours at 80° C. under vacuum (0.1 mm Hg), followed by 32 hours at 110° C. to remove residual monomers. A weight loss of 1.8% was observed.

The polymer had a melting point of about 190° C. by Fisher-Johns, and an inherent viscosity of 1.62 dL/g in HFIP. The molar ratio of PCL/PDS/PGA ratio was found to be 25/8/67 by $^1$H NMR.

Example 5

Synthesis of a segmented polymer composed of ε-caprolactone and p-dioxanone at a 20:80 (mol/mol) composition with 60 mole % glycolide where the center segment is ε-caprolactone, and p-dioxanone, with end segments of glycolide To a flame dried 250 mL two neck flask, 9.1 gm (0.08 mole) ε-caprolactone, 32.7 gm (0.32 mole) of p-dioxanone, 0.114 mL (1.2 mmole/mole of total monomer) of diethylene glycol and 0.067 mL of stannous octoate (0.33 molar solution in toluene) were added. The flask was fitted with a flame dried mechanical stirrer and an adapter. The reactor was then purged three times before being vented with nitrogen. The reaction mixture was then heated to 160° C. under nitrogen for about 2 hours. A sample was taken for characterization and the bath temperature was lowered to 110° C. for 6 hours. A second sample was taken for characterization.

69.6 gm (0.60 mole) of molten glycolide was then added to the prepolymer in the reaction flask. The temperature was then raised to 200° C. for one hour.

The polymer was isolated, ground, and dried for 16 hours at 80° C. under vacuum (0.1 mm Hg), followed by 32 hours at 110° C. to remove residual monomers. The polymer had a melting point of about 211° C. by DSC, and an inherent viscosity of 1.63 dL/g in HFIP.

Example 6

Synthesis of a segmented polymer composed of ε-caprolactone and p-dioxanone at a 35:65 (mol/mol) composition with 60 mole % glycolide where the center segment is ε-caprolactone and p-dioxanone, with end segments of glycolide To a flame dried 250 mL three neck flask, 16.0 gm (0.14 mole) of ε-caprolactone, 26.5 gm (0.26 mole) of p-dioxanone, 0.114 mL (1.2 mmole/mole of total monomer) of diethylene glycol and 0.067 mL stannous octoate (0.33 molar solution in toluene) were added. The flask was fitted with a flame dried mechanical stirrer and an adapter. The reactor was then purged three times before being vented with nitrogen. The reaction mixture was heated to 160° C. under nitrogen for about 2 hours. A sample was taken for characterization and the bath temperature was lowered to 110° C. for 6 hours. A second sample was taken for characterization.

69.6 gm (0.60 mole) of molten glycolide was then added to the prepolymer in the reaction flask. The temperature was then raised to 200° C. for one hour at this temperature.

The polymer was isolated, ground, and dried for 16 hours at 80° C. under vacuum (0.1 mm Hg), followed by 32 hours at 110° C. to remove residual monomers. The polymer had an inherent viscosity of 1.63 dL/g in HFIP.

Example 7

Synthesis of a segmented polymer composed of ε-caprolactone and p-dioxanone at a 80:20 (mol/mol) composition with 60 mole % glycolide where the center segment is ε-caprolactone, p-dioxanone and glycolide, with end segments of glycolide To a flame dried 250 mL three neck flask, 36.5 gm (0.32 mole) of ε-caprolactone, 8.2 gm (0.08 mole) of p-dioxanone, 34.8 gm (0.30 mole) of glycolide, 0.114 mL (1.2 mmole/mole of total monomer) of diethylene glycol and 0.067 mL of stannous octoate (0.33 molar solution in toluene) were added. The flask was fitted with a flame dried mechanical stirrer and an adapter. The reactor was then purged three times before being vented with nitrogen. The reaction mixture was heated to 110° C. under nitrogen for about 30 minutes, then raised to 160° C. for about 30 minutes, followed by 190° C. for an additional 16 hours. A second sample was taken for characterization.

34.8 gm (0.30 mole) of molten glycolide was then added to the prepolymer in the reaction flask. The temperature was then raised to 200° C. for one hour.

The polymer was isolated, ground, and dried for 16 hours at 80° C. under vacuum (0.1 mm Hg), followed by 32 hours at 110° C. to remove residual monomers. The polymer had an inherent viscosity of 1.80 dL/g in HFIP.

Example 8

Synthesis of a segmented polymer composed of ε-caprolactone and p-dioxanone at a 65:35 (mol/mol) composition with 60 mole % glycolide where the center segment is ε-caprolactone, p-dioxanone and glycolide, with end segments of glycolide To a flame dried 250 mL three neck flask, 29.7 gm (0.26 mole) of ε-caprolactone, 14.3 gm (0.14 mole) of p-dioxanone, 34.8 gm (0.30 mole) of glycolide, 0.114 mL (1.2 mmole/mole of total monomer) of diethylene glycol and 0.067 mL of stannous octoate (0.33 molar solution in toluene) were charged. The flask was fitted with a flame dried mechanical stirrer and an adapter. The reactor was then purged three times before being vented with nitrogen. The reaction mixture was heated to 110° C. under nitrogen for about 30 minutes, then raised to 160° C. for about 30 minutes at 160° C., followed by 190° C. for about 16 hours at 190° C. A second sample was taken for characterization.

34.8 gm (0.30 mole) of molten glycolide was then added to the prepolymer in the reaction flask. The temperature was then raised to 200° C. for one hour.

The polymer was isolated, ground, and dried for 16 hours at 80° C. under vacuum (0.1 mm Hg), followed by 32 hours at 110° C. to remove residual monomers. The polymer had an inherent viscosity of 1.69 dL/g in HFIP.

TABLE 4

| In-vitro BSR (%) | Example 3 size 4/0 | Example 4 size 4/0 | VICRYL ®-RAPIDE ® size 6/0 |
| --- | --- | --- | --- |
| Zero-day | 100 | 100 | 100 |
| 7 days | 44 | 45 | 60 |
| 12 days | 17 | 19 | 25 |

We claim:

1. An absorbable, biocompatible single phase copolymer comprising:
    about 95 mole percent to about 30 mole percent of a prepolymer containing repeating units of p-dioxanone and ε-caprolactone, wherein the molar ratio of ε-caprolactone to p-dioxanone in the prepolymer is about 95:5 to about 5:95, the caprolactone, wherein the molar ratio of ε-caprolactone to p-dioxanone in the prepolymer is about 95:5 to about 5:95, the prepolymer also contains from about 3 mole percent to about 35 mole percent glycolide and the inherent viscosity of the prepolymer is in the range of from about 0.6 g/dL to about 2 g/dL; copolymerized within the range of from about 5 mole percent to about 70 mole percent of repeating units of glycolide; wherein the ratio of glycolide to ε-caprolactone is selected to provide a single phase copolymer having a Young's modulus less than 185,000 psi.

2. The segmented polymer of claim 1 wherein the polymer has a molecular weight such that the inherent viscosity is from about 1 dL/g to about 3.0 dL/g as measured in HFIP at a concentration of 0.1 g/dL.

3. The segmented polymer of claim 1 wherein the polymer comprises about 10 mole percent to about 60 mole percent of repeating units of glycolic esters, and wherein the polymer comprises about 90 mole percent to about 40 mole percent of repeating units of p-dioxanone and ε-caprolactone, wherein the molar ratio of ε-caprolactone to p-dioxanone is about 90:10 to about 10:90.

4. The segmented polymer of claim 1 wherein the repeating units of glycolic esters comprise about 10 mole percent to about 45 mole percent, and wherein the repeating units of p-dioxanone and ε-caprolactone comprise about 90 mole percent to about 55 mole percent of the polymer, wherein the molar ratio of ε-caprolactone to p-dioxanone is about 80:20 to about 20:80.

5. An absorbable medical device formed from an absorbable, biocompatible single phase copolymer comprising:
    about 95 mole percent to about 30 mole percent of a prepolymer containing repeating units of p-dioxanone and ε-caprolactone, wherein the molar ratio of ε-caprolactone to p-dioxanone is about 95:5 to about 5:95, the prepolymer also contains from about 3 mole percent to about 35 mole percent glycolide and the inherent viscosity of the prepolymer is in the range of from about 0.6 g/dL to about 2 g/dL;
    copolymerized within the range of from about 5 mole percent to about 70 mole percent of repeating units of glycolide wherein the ratio of glycolide to ε-caprolactone is selected to provide a single phase copolymer having a Young's modulus less than 185,000 psi.

6. An absorbable medical device of claim 5 wherein additionally present in the prepolymer is glycolide.

7. The absorbable medical device of claim 6 the segmented polymer comprising:
    in the range of from about 10 mole percent to about 45 mole percent of repeating units of glycolide; and,
    in the range of from about 90 mole percent to about 55 mole percent of repeating units of p-dioxanone and ε-caprolactone.

8. The absorbable medical device of claim 5 wherein the medical device is selected from the group consisting of burn dressings, hernia patches, medicated dressings, fascial substitutes, gauze, fabric, sheet, felt, sponge for liver hemostasis, gauze bandages, arterial graft or substitutes, bandages for skin surfaces, burn dressings, bone substitutes, needles, intrauterine devices, tubes, surgical instruments, vascular implants, vascular supports, vertebral discs, extracorporeal tubing, artificial skin, stents, suture anchors, injectable defect fillers, preformed defect fillers, tissue adhesives, tissue sealants, bone waxes, cartilage replacements, hemostatic barriers, tissue scaffolds, monofilament sutures and braided sutures.

9. A process for producing a single phase copolymer comprising the steps of:
    a) polymerizing p-dioxanone, ε-caprolactone and glycolide in the presence of a catalytically effective amount of catalyst and an initiator at a sufficient temperature and for a sufficient period of time to yield a p-dioxanone-co-ε-caprolactone-co-glycolide prepolymer having an inherent viscosity in the range of from about 0.6 g/dL to about 2 g/dL; and,
    b) polymerizing the prepolymer with about 5 mole percent to about 70 mole percent glycolide at a sufficient temperature and for a sufficient amount of time to form a segmented polymer wherein the ratio of glycolide to ε-caprolactone is selected to provide a single phase copolymer.

10. The process of claim 9 for producing a segmented polymer wherein the temperature for the initial polymerization is about 100° C. to less than 190° C. and the time is about 2 to about 8 hours and the temperature for the second step of the polymerization is about 160° C. to about 230° C., and the time is about one-half hour to about 4 hours.

11. The process of claim 9 wherein the segmented polymer comprises:

in the range of from about 10 mole percent to about 60 mole percent of repeating units of glycolide and, in the range of from about 90 mole percent to about 40 mole percent of repeating units of p-dioxanone and ε-caprolactone.

12. The process of claim 9 wherein the segmented polymer comprises:

in the range of from about 10 mole percent to about 45 mole percent of repeating units of glycolide and, in the range of from about 90 mole percent to about 55 mole percent of repeating units of p-dioxanone and ε-caprolactone.

13. A medical device coated with a single phase copolymer comprising about 95 mole percent to about 30 mole percent of repeating units of p-dioxanone and ε-caprolactone, wherein the molar ratio of ε-caprolactone to p-dioxanone is about 95:5 to about 5:95, the prepolymer also contains from about 3 mole percent to about 35 mole percent glycolide and the inherent viscosity of the prepolymer is in the range of from about 0.6 g/dL to about 2 g/dL; copolymerized within the range of from about 5 mole percent to about 70 mole percent of repeating units of glycolic esters; and wherein the ratio of glycolide to ε-caprolactone is selected to provide a single phase copolymer having a Young's modulus is less than 185,000 psi.

14. The medical device of claim 13 wherein the medical device is a suture.

15. The medical device of claim 13 wherein the medical device is a needle.

16. A drug delivery matrix comprising a drug and a single phase copolymer formed from a prepolymer of about 95 mole percent to about 30 mole percent of repeating units of p-dioxanone and ε-caprolactone, wherein the molar ratio of ε-caprolactone to p-dioxanone is about 95:5 to about 5:95, the prepolymer also contains from about 3 mole percent to about 35 mole percent glycolide and the inherent viscosity of the prepolymer is in the range of from about 0.6 g/dL to about 2 g/dL; copolymerized within the range of from about 5 mole percent to about 70 mole percent of repeating units of glycolide; and wherein the ratio of glycolide to ε-caprolactone is selected to provide a single phase copolymer having a Young's modulus is less than 185,000 psi.

* * * * *